United States Patent
Caspary et al.

(10) Patent No.: US 11,918,588 B2
(45) Date of Patent: Mar. 5, 2024

(54) NEURONAL NICOTINIC ACETYLCHOLINE RECEPTOR PARTIAL AGONISTS AS THERAPEUTICS FOR CHRONIC TINNITUS

(71) Applicant: Board of Trustees of Southern Illinois University, Springfield, IL (US)

(72) Inventors: Donald Caspary, Springfield, IL (US); Thomas Brozoski, Springfield, IL (US); Brandon Cox, Springfield, IL (US)

(73) Assignee: Board of Trustees of Southern Illinois University, Springfield, IL (US)

( * ) Notice: Subject to any disclaimer, the term of this patent is extended or adjusted under 35 U.S.C. 154(b) by 235 days.

(21) Appl. No.: 17/428,164

(22) PCT Filed: Feb. 6, 2020

(86) PCT No.: PCT/US2020/017002
§ 371 (c)(1),
(2) Date: Aug. 3, 2021

(87) PCT Pub. No.: WO2020/163588
PCT Pub. Date: Aug. 13, 2020

(65) Prior Publication Data
US 2022/0088028 A1 Mar. 24, 2022

Related U.S. Application Data

(60) Provisional application No. 62/802,763, filed on Feb. 8, 2019.

(51) Int. Cl.
*A61K 31/55* (2006.01)
*A61K 31/4427* (2006.01)
*A61P 27/16* (2006.01)

(52) U.S. Cl.
CPC .......... *A61K 31/55* (2013.01); *A61K 31/4427* (2013.01); *A61P 27/16* (2018.01)

(58) Field of Classification Search
CPC ...... A61K 31/55; A61K 31/4427; A61P 27/16
See application file for complete search history.

(56) References Cited

FOREIGN PATENT DOCUMENTS

| WO | 0072835 A3 | 12/2000 |
| WO | 2010028769 A1 | 3/2010 |
| WO | WO 2010/028769 | * 3/2010 |

OTHER PUBLICATIONS

Turner et al., "Nicotinic Partial Agonists Varenicline and Sazetidine-A Have Differential Effects on Affective Behavior", The Journal of Pharmacology and Experimental Therapeutics, 2010, pp. 665-672, vol. 334, No. 2, The American Society for Pharmacology and Experimental Therapeutics.
Toronto Research Chemicals, Product Description: Sazetidine A Hydrochloride. 2017; p. 3, Chemical Name; p. 3, Applications.
International Search Report and Written Opinion from the corresponding International Patent Application No. PCT/US2020/017002, dated Mar. 20, 2020.

* cited by examiner

*Primary Examiner* — Marcos L Sznaidman
(74) *Attorney, Agent, or Firm* — Greer, Burns & Crain, Ltd.; Steven P. Fallon

(57) ABSTRACT

A method for treating a subject with symptoms of tinnitus and pharmaceutical compositions for treating tinnitus, the pharmaceutical compositions comprising one or more of the following: sazetidine, a pharmaceutically acceptable salt of sazetidine, varenicline, a pharmaceutically acceptable salt of varenicline, or any combination thereof.

15 Claims, 7 Drawing Sheets

NEURONAL NICOTINIC ACETYLCHOLINE RECEPTOR PARTIAL AGONISTS AS THERAPEUTICS FOR CHRONIC TINNITUS

CROSS-REFERENCE TO RELATED APPLICATIONS

This application claims the benefit of priority to U.S. Provisional Patent Application No. 62/802,763 filed Feb. 8, 2019, the entire disclosure of which is herein incorporated by reference.

STATEMENT REGARDING FEDERALLY SPONSORED RESEARCH

This invention was made with government support under grant number N00014-16-1-2306 awarded by the Office of Naval Research. The government has certain rights in the invention.

TECHNICAL FIELD

This disclosure relates to compositions and methods for treating tinnitus.

BACKGROUND

Tinnitus is defined as a phantom sound (ringing in the ears) that can significantly affect the quality of life for those experiencing it. The most common cause of tinnitus is high-level noise exposure. Although chronic tinnitus is present in 10 to 15 percent of the population, only 5 to 10 percent of those affected are bothered by the sensation. This is equivalent to 4.4 to 8.7 million people in North America alone. People not bothered by their tinnitus can readily report its characteristics, such as, tonality, location (e.g., right ear), and persistence. When questioned further, however, these people communicate that most of the time, they are not aware of their tinnitus. In other words, these individuals rarely attend to their tinnitus. In contrast, those who seek treatment for tinnitus report that it persistently and disruptively intrudes on their daily experience. They may also experience depression, anxiety, sleep disturbances, inability to concentrate, fatigue, and sometimes they commit suicide. For these individuals, their attention appears inextricably drawn to their tinnitus. The magnitude of tinnitus distress may relate to attention fixed on this phantom auditory percept. Given this dynamic, strategies for treating the attentional aspects of tinnitus might be as important as treatment of the tinnitus sensation itself. To our knowledge, no pharmaceutical treatment using this approach has ever been tested.

It has been hypothesized that individuals with tinnitus have a portion of their attentional resources, which are finite, bound to their tinnitus and as a result are less capable of accurately processing acoustic information. It is also possible that tinnitus interferes with the control of attention, thus enabling a pathological focus on the tinnitus sensation. Tinnitus sufferers report difficulty concentrating and the inability to direct their attention away from their tinnitus. However, when distracted by an engaging task or an attention-demanding task, tinnitus is generally less obtrusive.

A number of human studies have shown that subjects with severe tinnitus perform at a lower level on attention-demanding tasks than do non-tinnitus controls. Using a classic selective attention task, the Stroop Test, subjects with chronic tinnitus underperformed non-tinnitus controls. More broadly, cognitive deficits observed in chronic tinnitus patients have been attributed to attention deficiencies. Even, the miss-match-negativity evoked response, often considered a lower level pre-attentive response, is attenuated in humans with chronic tinnitus. Attentive integration may also be impacted by tinnitus, with functional imaging studies showing that cortical integrative networks connecting primary auditory and visual areas are altered in subjects with chronic tinnitus. Behavioral approaches used to treat tinnitus, such as tinnitus retraining therapy and similar methods used to treat chronic pain, have focused on directing attention away from the adverse sensory percept.

SUMMARY

In one aspect, the present disclosure provides a method for treating a subject in need of treatment for tinnitus, the method comprising: administering to the subject a pharmaceutical composition comprising one or more pharmaceutically acceptable excipients and a therapeutically effective amount of sazetidine, varenicline, a pharmaceutically acceptable salt of sazetidine, a pharmaceutically acceptable salt of varenicline, or any combination thereof. In some embodiments, the method may be performed with the pharmaceutical composition which contains sazetidine and/or varenicline in the form of tartarate, lactate, citrate, succinate, bisulfate, sulfate, phosphonate, hydrochloride, monohydrogen phosphate, dihydrogen phosphate, or any combination thereof.

In the present treatment methods, the pharmaceutical composition may be administered as an oral formulation, as nasal drops or a nasal spray, as ear drops or an ear spray, topically, by intravenous injection, by intramuscular injection or by subcutaneous injection. One of the preferred routes of administration is oral administration.

In some preferred embodiments of the treatment method, the pharmaceutical composition comprises sazetidine and/or the pharmaceutically acceptable salt thereof. In some other preferred embodiments of the method, the pharmaceutical composition comprises varenicline and/or the pharmaceutically acceptable salt thereof. In further preferred embodiments of the method, the pharmaceutical composition may comprise sazetidine hydrochloride and/or it may comprise varenicline tartarate.

The present treatment methods can be conducted with the pharmaceutical composition which comprises sazetidine and/or the pharmaceutically acceptable salt thereof, and the subject is administered a dose equivalent to from about 0.1 mg to about 2 mg of sazetidine free base per day. In preferred embodiments, the present treatment methods can be conducted with the pharmaceutical composition which comprises sazetidine and/or the pharmaceutically acceptable salt thereof and the subject is administered a dose equivalent to 0.1 mg, 0.2 mg, 0.3 mg, 0.4 mg, 0.5 mg, 0.6 mg or 0.7 mg of sazetidine free base per day.

The present treatment methods can be also conducted with the pharmaceutical composition which comprise varenicline and/or the pharmaceutically acceptable salt thereof and the subject is administered a dose equivalent to from about 0.1 mg to about 2 mg of varenicline free base per day. In some preferred embodiments of the treatment method, the pharmaceutical composition comprises varenicline and/or the pharmaceutically acceptable salt thereof and the subject is administered a dose equivalent to 0.1 mg, 0.2 mg, 0.3 mg, 0.4 mg, 0.5 mg, 0.6 mg or 0.7 mg of varenicline free base per day.

In some of the present methods, the pharmaceutical composition can be administered orally in the form of a tablet, powder, a capsule, lozenges, chewables, syrup, or aerosol. In alternative, the pharmaceutical composition can be administered as nasal drops or spray or as ear drops or spray. The present methods may further comprise monitoring the subject for adverse side effects.

In another aspect, the present disclosure provides a pharmaceutical composition for use in treating tinnitus, wherein the pharmaceutical composition comprises one or more pharmaceutically acceptable excipients and wherein the composition is characterized in that it comprises a therapeutically effective amount for treating tinnitus of an active compound wherein the active compound is one or more of the following: sazetidine, varenicline, a pharmaceutically acceptable salt of sazetidine, a pharmaceutically acceptable salt of varenicline, a sazetidine prodrug, a varenicline prodrug, a solvate of sazetidine, a solvate of varenicline, a hydrate of sazetidine, a hydrate of varenicline, or any combination thereof. Some of the preferred pharmaceutical compositions may comprise sazetidine and/or the pharmaceutically acceptable salt thereof in the therapeutically effective amount equivalent to from about 0.1 mg to about 2 mg of sazetidine free base per one dose. Some of the preferred pharmaceutical compositions may comprise varenicline and/or the pharmaceutically acceptable salt thereof in the effective amount equivalent to from about 0.1 mg to about 2 mg of varenicline free base per one dose. Particularly preferred pharmaceutical compositions include those which comprise varenicline tartarate and/or sazetidine hydrochloride.

The pharmaceutical compositions in this disclosure include those formulated as a tablet, gel capsule, powder, capsule, lozenge, chewable, syrup, a solution for oral consumption, emulsion, aerosol, nasal drops, nasal spray, ear drops, ear spray or as an injectable formulation.

DETAILED DESCRIPTION

Figure 1:
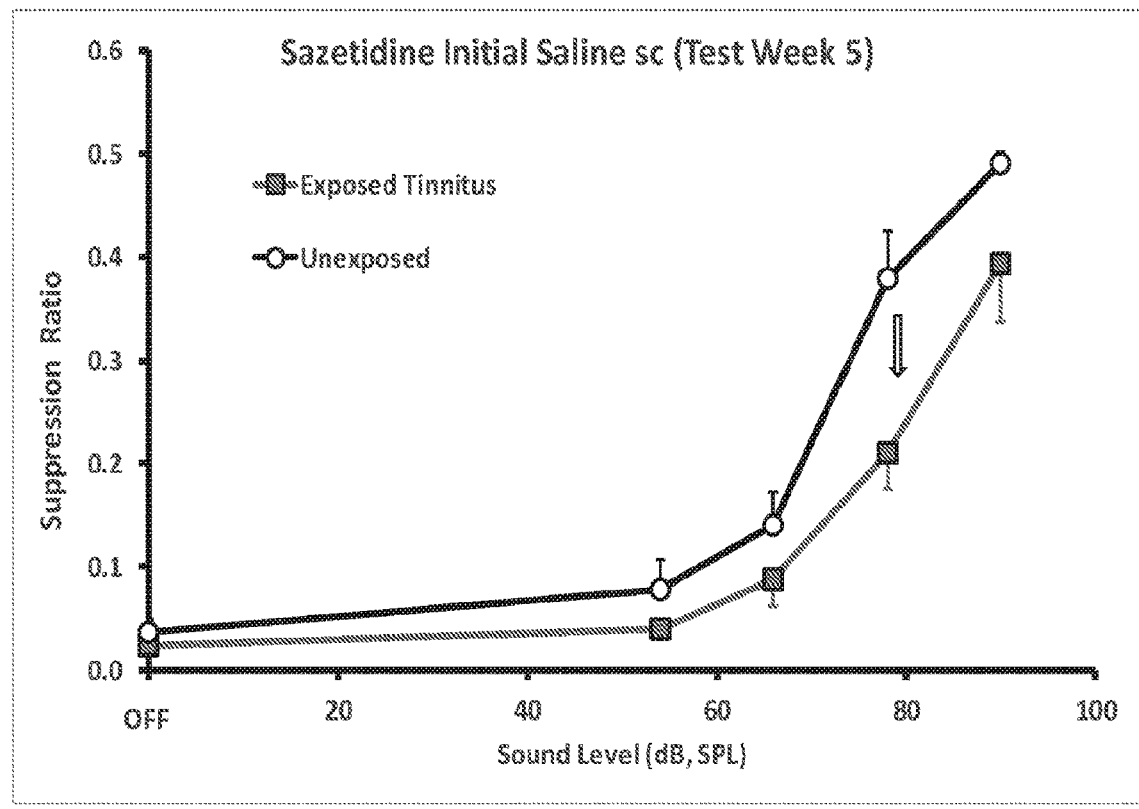
FIG. 1 illustrates significant evidence of tinnitus (arrow indicating down-shifted function) five weeks following sound exposure and prior to the first drug dose. Animals with behavioral evidence of tinnitus are compared to control non-sound exposed animals. Initial tinnitus tests used saline as the drug vehicle. For this and all subsequent figures, suppression curves used a 20 kHz background sound and represent average behavioral data from three sessions. The difference between the unexposed control and exposed-tinnitus group function was significant as indicated by a mixed analysis of variance ($F_{1,32}=14.05$, $p=0.0007$), where F is the statistic (subscript, degrees of freedom) and p is the probability of a random-chance difference.

Brain circuits critically involved in the control of attention, arousal, and learning utilize the neurotransmitter acetylcholine (ACh) and project to sensory structures including the auditory cortex and auditory thalamus (medial geniculate body, MGB) in animal subjects that include rats, mice, primates, humans, dogs, cats, chinchillas and other mammals (collectively referred to as subject or subjects).

In rats, the pedunculopontine tegmental nucleus (PPTg) projects to the MGB while basal forebrain cholinergic neurons project to auditory cortex (AI). Both pathways release ACh acting at neuronal nicotinic acetylcholine receptors (nAChRs) and muscarinic receptors. Basal forebrain cholinergic neurons are shown to have a direct role in enhancing responses to novel/salient acoustic stimulation in AI, with similar mechanisms suggested to be present in auditory thalamus (MGB) Phantom sounds/tinnitus have no environmental reality and thus may be perceived as novel. Emergent models of tinnitus suggest that increased cholinergic tone in MGB and AI, originating from PPTg and basal forebrain projections, would result in changes in thalamo-cortical/corticothalamic activity causing a subset of neurons to switch to burst mode/higher frequency oscillations. This neural activity results in increased attention focused on the novel/deviant phantom sound.

The nAChR is a cell membrane channel made up of five $\alpha$ and $\beta$ subunits, where different combinations of $\alpha$s and $\beta$s form subtypes of nAChRs. All known nAChRs are permeable to sodium and calcium resulting in depolarization of the pre- or post-synaptic membrane. There is a large amount of evidence showing that nAChRs exist as presynaptic receptors where they modulate the release of different transmitters and hormones. Presynaptic nAChRs have been implicated in modulating the release of glutamate and GABA, as well as ACh.

nAChR ligands can be classified as agonists, partial agonists, competitive antagonists, and non-competitive antagonists. Agonists and partial agonists bind to the same nAChR ligand binding site as ACh causing a conformational change that leads to opening of the channel allowing entry of calcium and sodium cations. Somewhat paradoxically, certain ligands bind the nAChR, opening the channel briefly and produce a prolonged desensitization, which renders the nAChR inoperative. When desensitized, the receptor cannot be activated by ACh, theoretically decreasing attention and potentially fixation on the tinnitus percept.

Based on the putative role of maladaptive attentional changes in the pathology of tinnitus, the role of the cholinergic system and its receptors in the pathology of tinnitus was examined. Acetylcholine (ACh) is a neuromodulator critically involved in the control of attention in the brainstem and in higher sensory and cognitive brain centers. One major class of cholinergic receptors is the neuronal nicotinic acetylcholine receptor (nAChR). This ionotropic receptor can increase activation of neurons and their terminal endings by allowing entry of sodium and calcium ions.

Compounds/drugs that act at nAChRs, known as ligands, can be classified as agonists (activators), partial agonists (partial activators), competitive antagonists (competitive blockers), and non-competitive antagonists (non-competitive blockers).

Activation of nAChRs can be more complicated because of a property called desensitization which occurs when a receptor is activated initially but then shuts down. Agonists and partial agonists bind to the same ligand binding site as the native neurotransmitter ACh and can cause conformational changes in the nAChR that leads to opening of the channel One consequence of nAChR conformational changes is desensitization which alters the brain's attentional functions.

Sazetidine A (also referred to as sazetidine or saz and administered herein as SC sazetidine) and varenicline are partial nAChR agonists with very high affinity for $\beta$2-containing nAChRs. Sazetidine and varenicline desensitize $\alpha 4\beta 2$ nAChRs at low nanomolar concentrations. Sazetidine is >20,000 fold more selective for $\alpha 4\beta 2$ nAChRs (the most common nAChRs found in the brain) compared to $\alpha 3\beta 4$ nAChRs which are prominent in the autonomic nervous system. Sazetidine A is 3,500-fold more selective for $\alpha 4\beta 2$ nAChRs relative to $\alpha 7$ nAChRs.

Varenicline, which is sold as Chantix® (Pfizer) for smoking cessation, is another high affinity nAChR desensitizing agonist that is selective for $\alpha 4\beta 2$ receptors. Unlike sazetidine-A, varenicline also has partial agonist actions at $\alpha 3\beta 4$ nAChRs (at lower affinity), and full agonist activity at $\alpha 7$ nAChRs. Varenicline is 4,000-5,000 fold more selective for $\alpha 4\beta 2$ nAChRs compared to $\alpha 3\beta 4$ or $\alpha 7$ nAChRs. Most studies with varenicline focus on smoking sensation; however, evidence suggests an efficacy similar to sazetidine-A in mouse models of pain and depression.

The chemical structure of sazetidine and its derivatives are known from U.S. Pat. No. 8,030,300, the entire disclosure of which is incorporated herein by reference.

Varenicline may be also referred to as 7,8,9,10-tetrahydro-6,10-methano-6H-pyrazino[2,3-h][3]-benzazepine. Varenicline and its pharmaceutically acceptable acid addition salts are disclosed in International Patent Publication WO 99/35131, published Jul. 15, 1999, the entire disclosure of which is herein incorporated by reference. Methods for making varenicline are described in U.S. Pat. No. 6,410,550, the entire disclosure of which is herein incorporated by reference.

In one aspect, the present disclosure provides a pharmaceutical composition for treating tinnitus, wherein the pharmaceutical composition comprises one or more pharmaceutically acceptable excipients and sazetidine and/or any pharmaceutically acceptable salt thereof.

In another aspect, the present disclosure provides a pharmaceutical composition for treating tinnitus, wherein the pharmaceutical composition comprises one or more pharmaceutically acceptable excipients and varenicline and/or any pharmaceutically acceptable salt thereof.

Examples of pharmaceutically acceptable salts thereof include, but not limited to, sazetidine or varenicline formulated as tartarate, lactate, citrate, succinate, bisulfate, sulfate, phosphonate, hydrochloride, mono- or dihydrogen phosphate or as any other non-toxic salt. A particularly preferred pharmaceutically acceptable salt of varenicline is varenicline tartarate. A particularly preferred pharmaceutically acceptable salt of sazetidine is dihydrochloride.

The pharmaceutical compositions for treating tinnitus of this disclosure may comprise one or more pharmaceutically acceptable excipients and a compound, wherein the compound is therapeutically active in treating tinnitus, and wherein the compound is sazetidine and/or varenicline.

In some pharmaceutical compositions of this disclosure, a therapeutically active sazetidine compound may comprise sazetidine free base. However, at least some present pharmaceutical compositions may also comprise a therapeutically active sazetidine compound in the form of a sazetidine prodrug, a pharmaceutically acceptable salt of sazetidine, a solvate of sazetidine and/or hydrate of sazetidine. Thus, it should be understood that the term "a composition comprising sazetidine" in this disclosure means that the composition comprises sazetidine in one or more of the following forms: free base, prodrug, pharmaceutically acceptable salt, solvate and/or hydrate.

In some pharmaceutical compositions of this disclosure, a therapeutically active varenicline compound may comprise varenicline free base. However, at least some present pharmaceutical compositions may also comprise a therapeutically active varenicline compound in the form of a varenicline prodrug, a pharmaceutically acceptable salt of varenicline, a solvate of varenicline and/or hydrate of varenicline. Thus, it should be understood that the term "a composition comprising varenicline" in this disclosure means that the composition comprises varenicline in one or more of the following forms: free base, prodrug, pharmaceutically acceptable salt, solvate and/or hydrate.

Some preferred pharmaceutical compositions of this disclosure comprise one or more pharmaceutically acceptable salts of sazetidine and/or varenicline.

The pharmaceutical compositions in this disclosure may comprise any amount of sazetidine and/or varenicline effective for treating tinnitus. In some embodiments, the pharmaceutical compositions comprise the active compound in an amount effective for treating tinnitus and equivalent to from about 0.1 mg to about 2 mg of sazetidine and/or varenicline per one dose of the pharmaceutical composition. In some preferred embodiments, the pharmaceutical compositions comprise the active compound in an amount which is equivalent to from about 0.2 mg to about 1 mg of sazetidine and/or varenicline per one dose of the pharmaceutical composition. In some preferred embodiments, the pharmaceutical compositions comprise the active compound in an amount which is equivalent to from about 0.1 mg to about 0.5 mg of sazetidine and/or varenicline per one dose of the pharmaceutical composition. In some preferred embodiments, the pharmaceutical compositions comprise the active compound in an amount which is equivalent to from about 0.1 mg to about 1 mg of sazetidine and/or varenicline per one dose of the pharmaceutical composition.

The amount of the active compound per dose may be further adjusted as needed prior to the treatment and/or during the treatment, taking into consideration, any of the following factors: 1) the route of administration, e.g. oral, parenteral, topical or nasal; 2) severity of tinnitus; 3) subject's response to the treatment; 4) subject's body weight; 5) subject's other underlining conditions, e.g. renal disease; and/or 6) subject's age.

Some preferred pharmaceutical compositions of this disclosure comprise varenicline tartarate or any other pharmaceutically acceptable salt of varenicline in an amount which is equivalent to from about 0.1 to about 1 mg of varenicline free base per one dose.

Some preferred pharmaceutical compositions comprise sazetidine hydrochloride or any other pharmaceutically acceptable salt of sazetidine in an amount which is equivalent to from about 0.1 to about 1 mg of sazetidine free base per one dose.

In addition to the active compound, the pharmaceutical compositions of this disclosure may comprise one or more pharmaceutically acceptable excipients. Such excipients may include one or more of the following without limitation: water, a buffer, a solvent, a diluent, a stabilizer, a gel-forming agent, a bulking agent also known as an inert filler, a binder, a surfactant, a disintegrating agent, a lubricant, a texturizer, a flavoring agent, a sweetener, a coloring agent, a wetting agent, a carrier, a emulsifier, or any mixture thereof. A particular selection of excipients may be adjusted as needed, depending on a route of administration and many other factors well known a person of skill. Typical excipients for oral solid formulations may include one or more of the following: calcium carbonate, starch, e.g. corn starch or potato starch, carboxymethylcellulose, hydropropylmethyl cellulose, gelatin, sucrose, lactose, glucose, mannitol, sodium citrate, glycerol, sodium carbonate, talc, microcrystalline cellulose, dibasic calcium phosphate, croscarmellose sodium, silicon dioxide, magnesium stearate and many others.

Oral liquid formulations may comprise water and/or other solvents, solubilizing agents and emulsifiers, such as for example, as ethyl alcohol, glycerol, oil, polyethylene glycol, sorbitol and/or its derivatives, and/or microcrystalline cellulose.

Typical excipients for injectable formulations, nasal drops and ear drops include a solvent, which may be sterile water or buffer, e.g. sterile saline.

Preferred formulations for the pharmaceutical compositions of this disclosure are oral. Accordingly, the pharmaceutical compositions of this disclosure can be formulated and administered as tablets, including film-coated tablets, capsules, including soft gel capsules and hard gel capsules, powder, lozenges, chewables, syrup, a solution, including drops, emulsion, aerosol or any other form suitable for oral consumption. A person of skill would further appreciate that while the oral route of administration is preferred, the pharmaceutical compositions of this disclosure can be also administered as intravenous, intramuscular or subcutaneous injections. In these methods, the pharmaceutical composition is formulated as an injectable solution or as a powder which can be dissolved in a suitable solvent, e.g. sterile normal saline, just prior to injections. If further embodiments of this disclosure, the pharmaceutical compositions can be administered as nasal or ear drops or sprays.

In further aspect, the present disclosure provides methods for treating a subject in need of treatment for tinnitus. The methods comprise administering to the subject one or more of the pharmaceutical compositions of this disclosure. The subject may be a mammal, and preferably, the subject may be a human patient in need of treatment for tinnitus.

In this disclosure, the term "treatment of tinnitus" means ameliorating at least partially and at least temporarily, e.g. for at least 2 hours, at least some of the symptoms of tinnitus.

In the tinnitus treatment methods of this disclosure, the pharmaceutical composition of this disclosure can be administered to the subject in need of tinnitus treatment orally, topically, nasally, via ear drops or spray, or parenterally. In the tinnitus treatment methods of this disclosure, the pharmaceutical composition of this disclosure can be administered in any effective dosage of sazetidine or varenicline. Preferably, suitable dosages include a dose equivalent to from about 0.1 mg to about 2 mg of sazetidine free base per day, and more preferably a dosage equivalent to from about 0.1 mg to about 1 mg of sazetidine free base per day, e.g. 0.1 mg, 0.2 mg, 0.3 mg, 0.4 mg, 0.5 mg, 0.6 mg or 0.7 mg per day. Suitable dosages also include a dose equivalent to from about 0.1 mg to about 2 mg of varenicline free base per day, and more preferably a dose equivalent to from about 0.1 mg to about 1 mg of varenicline free base per day, e.g. 0.1 mg, 0.2 mg, 0.3 mg, 0.4 mg, 0.5 mg, 0.6 mg or 0.7 mg per day. It will be further appreciated that a dosage can be further adjusted as may be needed, for example, depending on subject's condition, weight and responsiveness to the drug. Accordingly, a treatment dosage can be lower or higher than the dosage ranges described above.

The subject may be administered one dose per day in one round of administration. For example, the subject may take a tablet daily. In some embodiments, the dose may be divided between several rounds of administration, e.g. 2, 3 or 4. For example, the total of 1 mg per day can be administered as a 0.5 mg tablet taken twice daily.

The preferred round of administration is oral. In the present treatment methods, the pharmaceutical composition of the present disclosure may be administered orally as a solid formulation or as a liquid formulation. Examples of oral solid formulations include, but not limited to, tablets, including coated tablets, gel capsules, including soft gel capsules and hard gel capsules, powder, capsules, lozenges and chewables. Examples of oral liquid formulations include, but not limited to, syrup, a solution, dispersion, emulsion, or aerosol.

In the present treatment methods, the subject may be further monitored for his/her responsiveness to the pharmaceutical composition as well for adverse side effects. The administration can start with a smaller dosage, e.g. 0.1 or 0.5 mg daily, and the dosage may be increased if needed.

In further aspect, the present disclosure provides kits for conducting the treatment methods of this disclosure. The kits comprise one or more of the pharmaceutical compositions of this disclosure which may be formulated in one or more forms provided in this disclosure, e.g. as tablets or sterile powder for parenteral administration, a dispensing container, e.g. a bottle or package, and instructions. The kit may further include one or more dispensing means.

Example 1

Methods

Unilaterally sound-exposed animals were used to study the effects of sazetidine on tinnitus. Experiments used an established behavioral psychoacoustic test to determine whether sazetidine could ameliorate tinnitus in subjects (rats) with behavioral evidence of tinnitus. Three months following sound-exposure, animals with tinnitus show consistent difficulty identifying silence. Sounds of varying intensity/levels were presented to sound-exposed (tinnitus) and unexposed (non-tinnitus control) subjects. The animals' behavior, quantified as a suppression ratio, indicated their level of tinnitus. Greater suppression, i.e., a decrease in lever pressing, indicates the presence of tinnitus. Treatment with sazetidine, 1 hour before testing, decreased tinnitus-related symptoms/lever pressing. Sound-exposed animals with behavioral evidence of tinnitus showed greater suppression than either sound-exposed animals without evidence of tinnitus or unexposed control animals.

The present study examined the potential therapeutic effect of sazetidine and varenicline to ameliorate tinnitus in rats with behavioral evidence of tinnitus. For two decades, an operant-behavior model has been used to investigate tinnitus pathology. In this model, animals are taught to attend closely to their auditory sensations using a conditioned suppression procedure: Animals lever press for food pellets in the presence of low-level background sounds, randomly punctuated by sound-off (silence) periods. Sound-off (silence) lever pressing earns food pellets but leads to a mild foot shock at the conclusion of the sound off presentation. The animals are therefore conditioned to stop lever pressing when the external sound is off, i.e., conditioned suppression. In this paradigm, the animals are conditioned to attend to their sound environment, and when tones of different frequencies and levels/intensities are substituted for some of the sound-off periods, the attendant behavior can be used to derive psychometric functions indicative of tinnitus.

Sixteen, 96-day old Long Evans rats (Envigo, Indianapolis, IN, USA) were anesthetized with a 1.7 percent isoflurane/02 mixture, placed in a head holder. A Fostex speaker (FT17H, Akashima, Japan) was attached to a 2 cm length of flexible tubing positioned at the entrance of the right ear canal. Eight randomly selected rats were unilaterally exposed once to band-limited noise for 1 hr, with a peak level of 120 dB (SPL) centered at 16 kHz, falling to ambient levels at 8 kHz and 24 kHz. During sound-exposure, the contralateral canal was obstructed by a canal-fitted plastic plug/tube from the contralateral speaker. Auditory brainstem responses (ABRs), which measure hearing, were obtained before and after exposure for pure tones at 8, 10, 12, 16, 20, 24, and 32 kHz, presented in 10 dB decrements between 95 and 5 dB (SPL re 20 Pa). Eight unexposed animals were similarly tested. Tinnitus testing began 3 months following sound-exposure and hearing-level determination.

Sazetidine A dihydrochloride (batch 2A/187725) was obtained in solid form, from Tocris Bioscience (Minneapolis, MN, USA). The drug was dissolved in sterile normal saline at a concentration of 2 mg/ml, or less, and administered as a subcutaneous injection (SC) 1 hour prior to behavioral testing.

Varenicline, varenicline tartrate, was purchased from Santa Cruz Biotechnology, Inc. (Dallas, TX, USA). The drug was dissolved in sterile normal saline at a concentration of 1 mg/ml, or less, and administered as a SC injection 1 hour prior to behavioral testing.

Sterile normal saline was considered a pharmaceutically acceptable carrier, but other pharmaceutically acceptable carriers may also be used as a substitute. All animals, unexposed controls and sound-exposed, were drug treated and tested in parallel. Maximum sub-cutaneous treatment volumes did not exceed 0.44 ml. Dose levels of 0.1, 0.5, and 1 mg/kg were tested for therapeutic effect, over a minimum of 3 consecutive days for each dose level. Washout periods of 1 to 5 weeks (5 test sessions per week) intervened between drug-testing, as required to recover pre-drug baseline tinnitus performance.

Prior to the start of drug testing, each group was optimized to five rats per group. The five rats with the best evidence of tinnitus were selected from the eight exposed, and five animals with the least evidence of tinnitus were selected from the eight unexposed controls. These optimized groups remained constant throughout all drug testing.

Given the sound-exposure procedure and experimental subjects (described above), 20 kHz test series are the optimum diagnostic for tinnitus. Group-average psychometric functions were derived from the 20 kHz test series. In this series the inserted test sound was 20 kHz tones presented at various intensity levels. The behavioral decision task for the animals was to discriminate between the test-sound presentations and background sound. Lever pressing was quantified using a relative rate measure, the suppression ratio (R). R was determined as a running measure for successive 1-min segments of each session using the formula $R=B/(A+B)$, where A was the number of lever presses in the preceding 1-min segment and B the number of lever presses in the current 1-min segment. R can vary between 0 and 1. A value of 0 is attained when lever pressing in the current minute is 0, a value of 0.5 when lever pressing in the current minute is equal to that of the previous minute, and a value of 1 when lever pressing in the previous minute is 0. R provided a running index of behavior, in 1-min epochs, and enabled a quantitative comparison between subjects as well as unbiased compilation of group data. R is a useful index of perceptual performance since it is sensitive to short-term behavioral effects, such as those produced by sensory events, but it is insensitive to gradual behavioral effects, such as those produced by changes in motivational status, for example, satiation.

In the context of the present procedure, it was expected that exposed rats with tinnitus would have lower R-values than unexposed rats, when tested with stimuli that resembled their tinnitus (tinnitus being the signal for potential foot shock). Typically a minimum of 5 sessions for each animal and for each sound condition (e.g., board band noise, 20 kHz tones, etc.) were averaged to derive individual and group psychophysical functions.

Results

Figure 2:
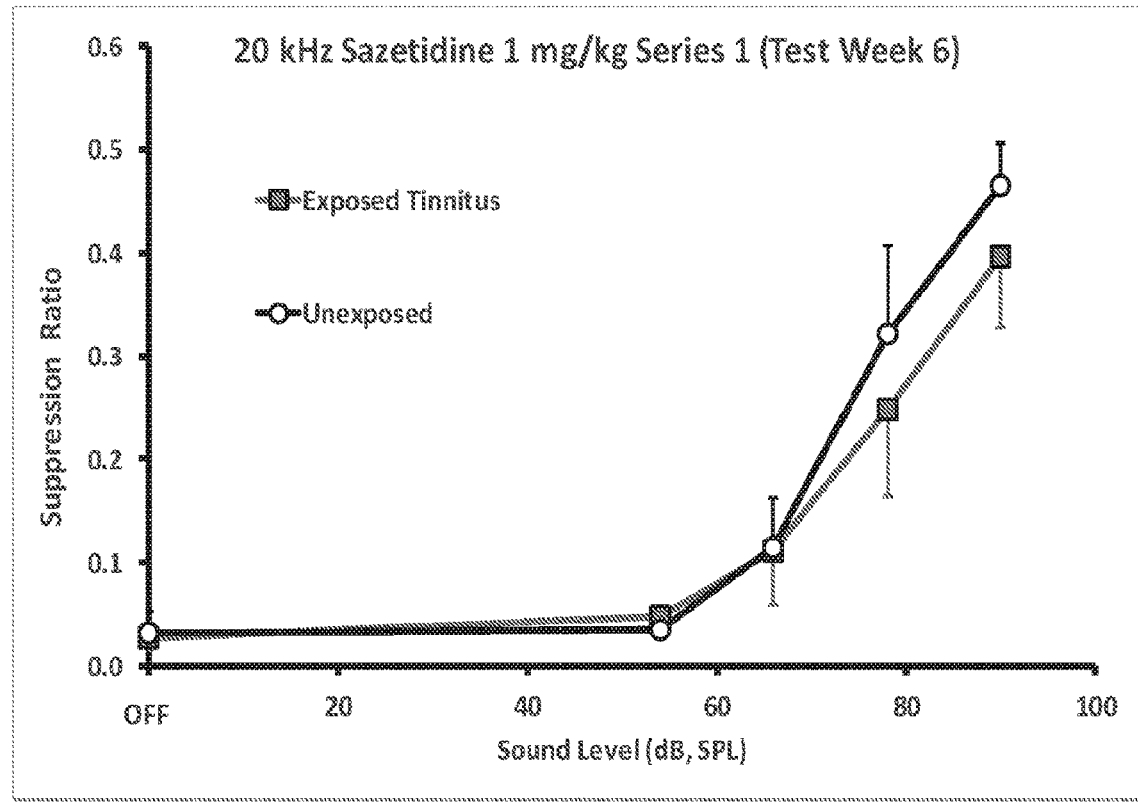
FIG. 2 shows the therapeutic effect following 1 mg/kg subcutaneous injection (or SC) of sazetidine. The suppression curve for tinnitus animals is no longer significantly different than the curve from the unexposed control animals without behavioral evidence of tinnitus ($F_{1,32}=0.66$; $p=0.4207$; $p'=0.6644$). $p'$ is the probability of a random-chance difference when Bonferroni corrected for repeated-test significance inflation.

Tinnitus was quantified by a comparison of the average psychophysical performance of the tinnitus group to that of the unexposed control group. Within the Figures, significance was determined using mixed ANOVAs, with treatment groups as the independent factor and sound level as the repeated-measures factor. Repeated test significance inflation was corrected with a Bonferroni posthoc test and reported as p'. For all behavioral tests for the presence or absence of tinnitus, both corrected and uncorrected p values are also reported in the figure legends. In regards to the saline series (FIGS. 2, 4, and 5), the animals were treated with saline which was used as the pharmaceutically acceptable carrier/drug vehicle.

Figure 3:
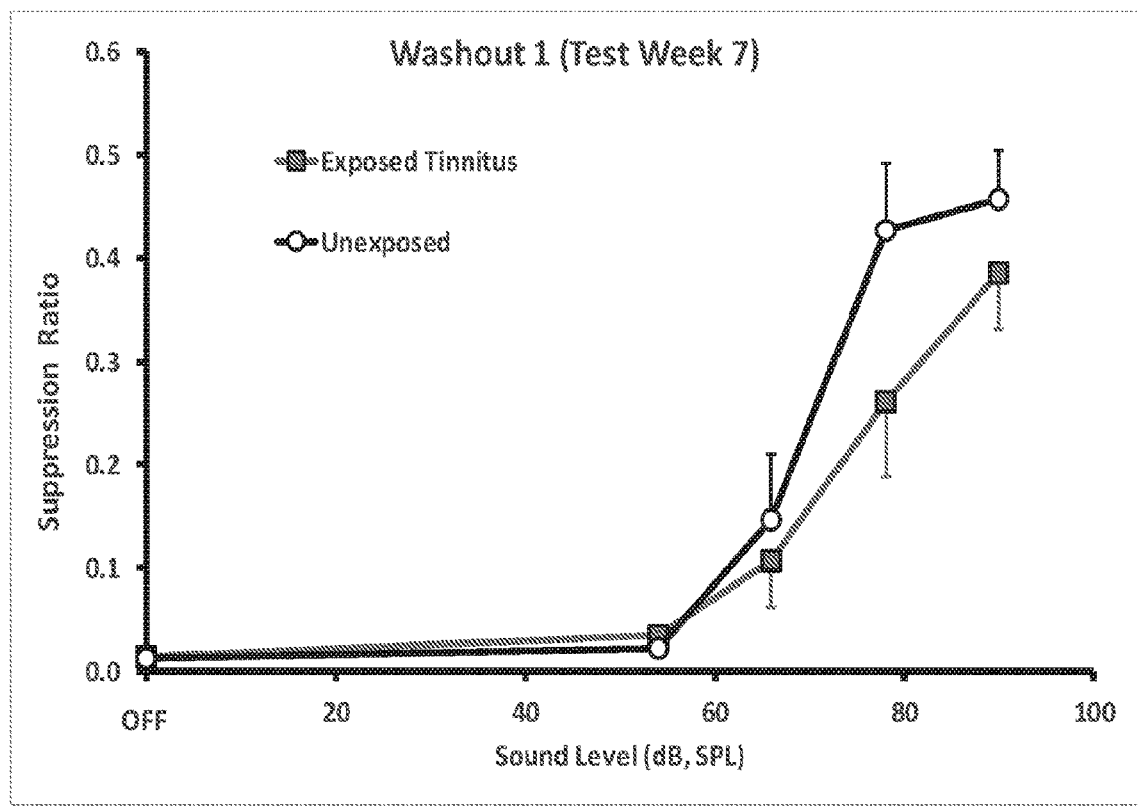
FIG. 3 shows data one week following initial sazetidine treatment, tinnitus animals remain similar to control, non-tinnitus animals. Statistical analysis: $F_{1,32}=3.42$, $p=0.0734$, $p'=0.2046$.
Figure 7:
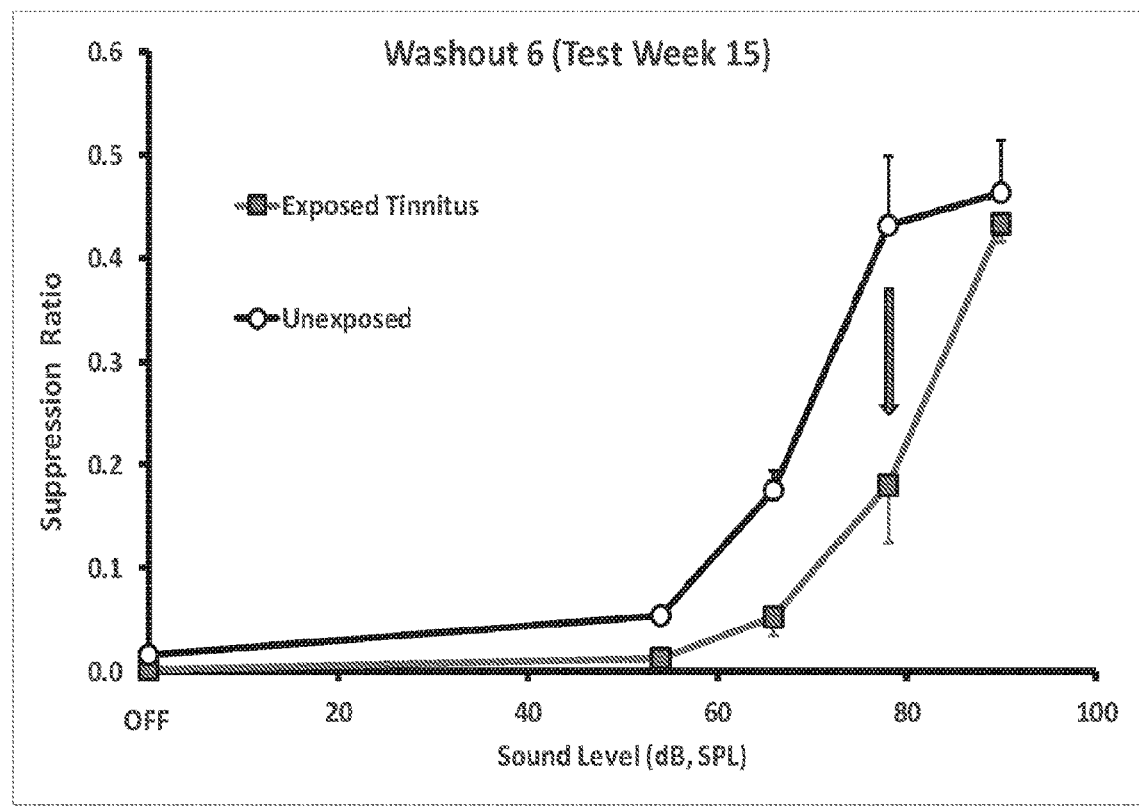
FIG. 7 shows the full return of tinnitus following a five-week washout period. Tinnitus animals were significantly different than the unexposed control group 15 weeks following induction the sound exposure inducing tinnitus. Statistical analysis: $F_{1,32}=18.40$, $p=0.0002$, $p'=0.0010$.

In the washout series (FIGS. 3, 7), the animals received no drug or vehicle. Sazetidine A, administered by SC injection, at 1 mg/kg, effectively and significantly decreased evidence of tinnitus (see FIGS. 2 and 11).

Figure 4:
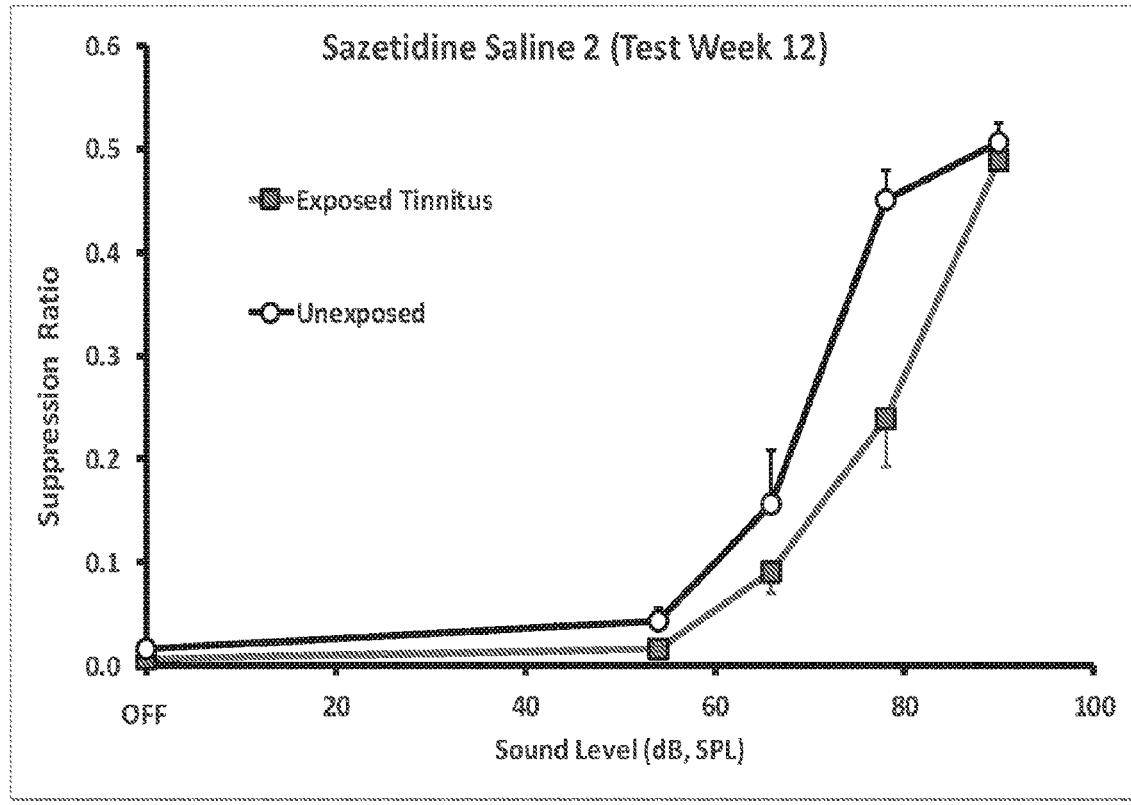
FIG. 4 shows that tinnitus animals are again statistically significantly different from the unexposed control animals, five weeks following initial sazetidine treatment. This result suggests a return of tinnitus. In this test, both groups received saline SC (vehicle) prior to tinnitus testing. Statistical analysis: $F_{1,32}=15.19$, $p=0.0005$, $p'=0.0019$.
Figure 5:
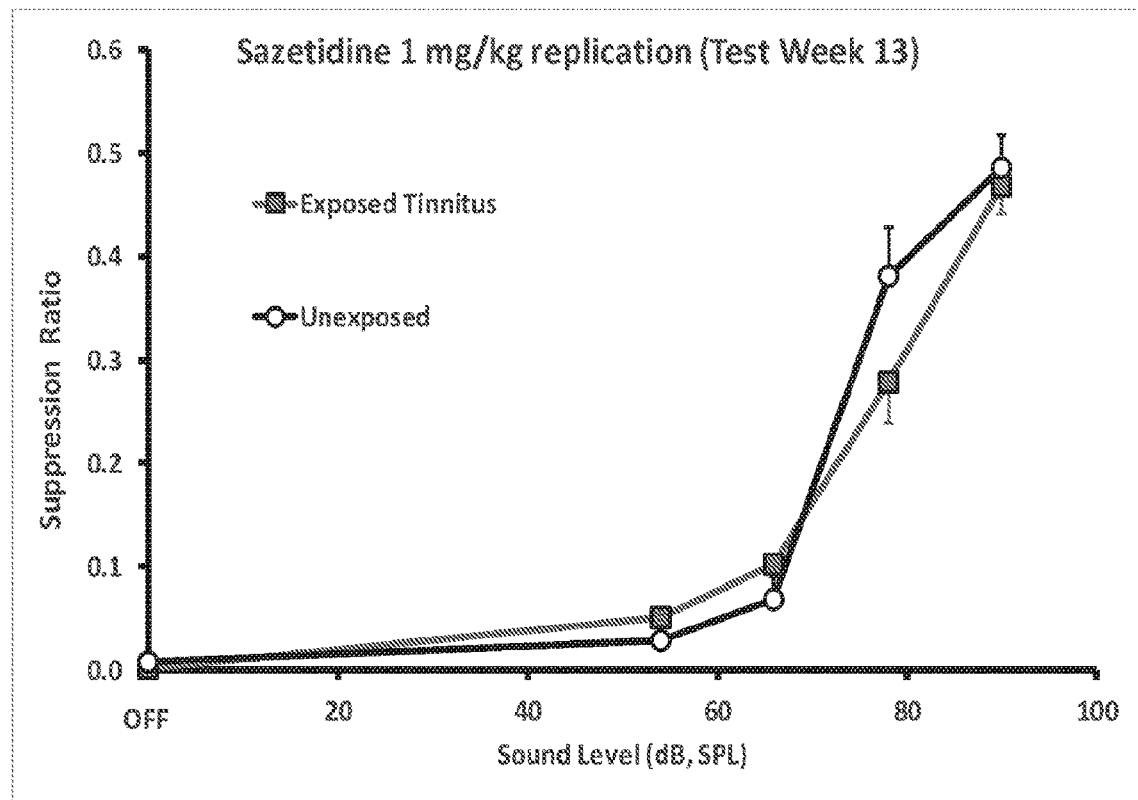
FIG. 5 shows the therapeutic effect of the second ($1^{st}$ replication) test following 1 mg/kg subcutaneous injection (or SC) of sazetidine. The suppression curve for animals with behavioral evidence of tinnitus is again no longer significantly different than that of the unexposed control animals. Statistical analysis: $F_{1,32}=0.49$, $p=0.4897$, $p'=0.9654$.
Figure 6:
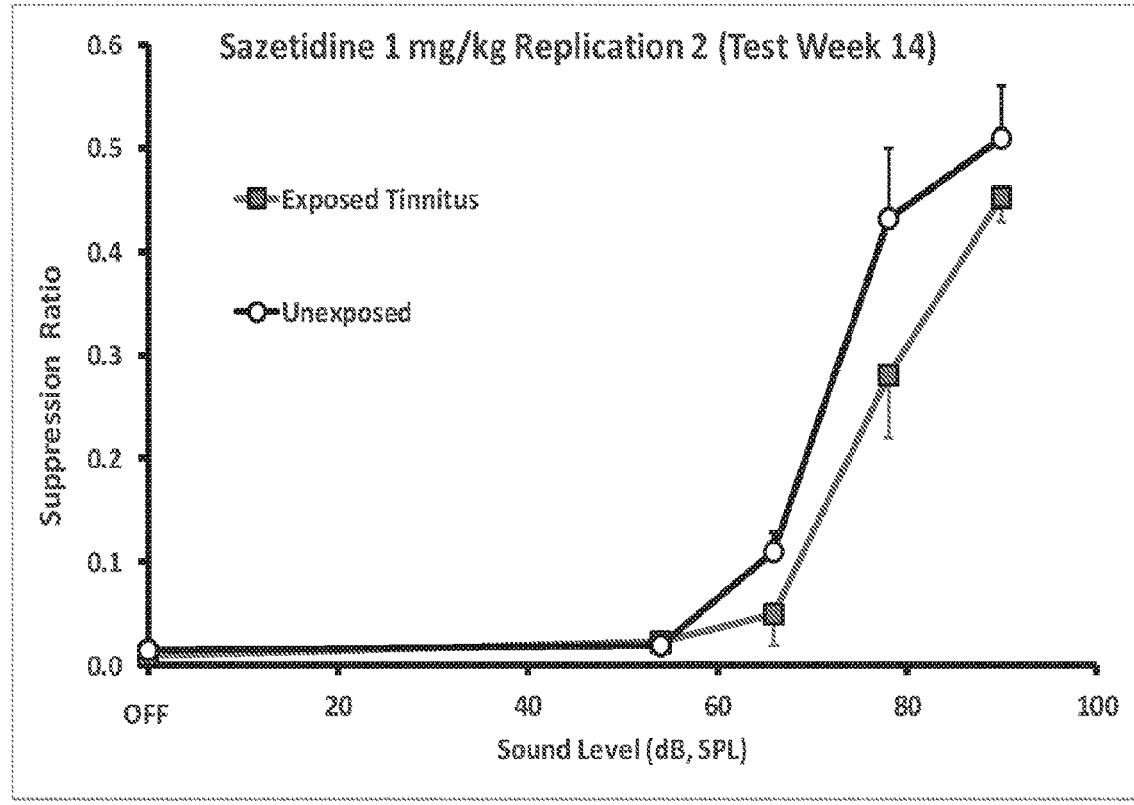
FIG. 6 shows a $3^{nd}$ sazetidine test to 1 mg/kg SC sazetidine (2nd replication) one week following the $1^{st}$ replication test. In this example, animals with behavioral evidence of tinnitus remain significantly different from the unexposed control group. No therapeutic effect was observed, perhaps suggesting drug tolerance after three repetitions of this dose in short succession. Statistical analysis: $F_{1,32}=5.62$, $p=0.0239$, $p'=0.1353$.
Figure 8:
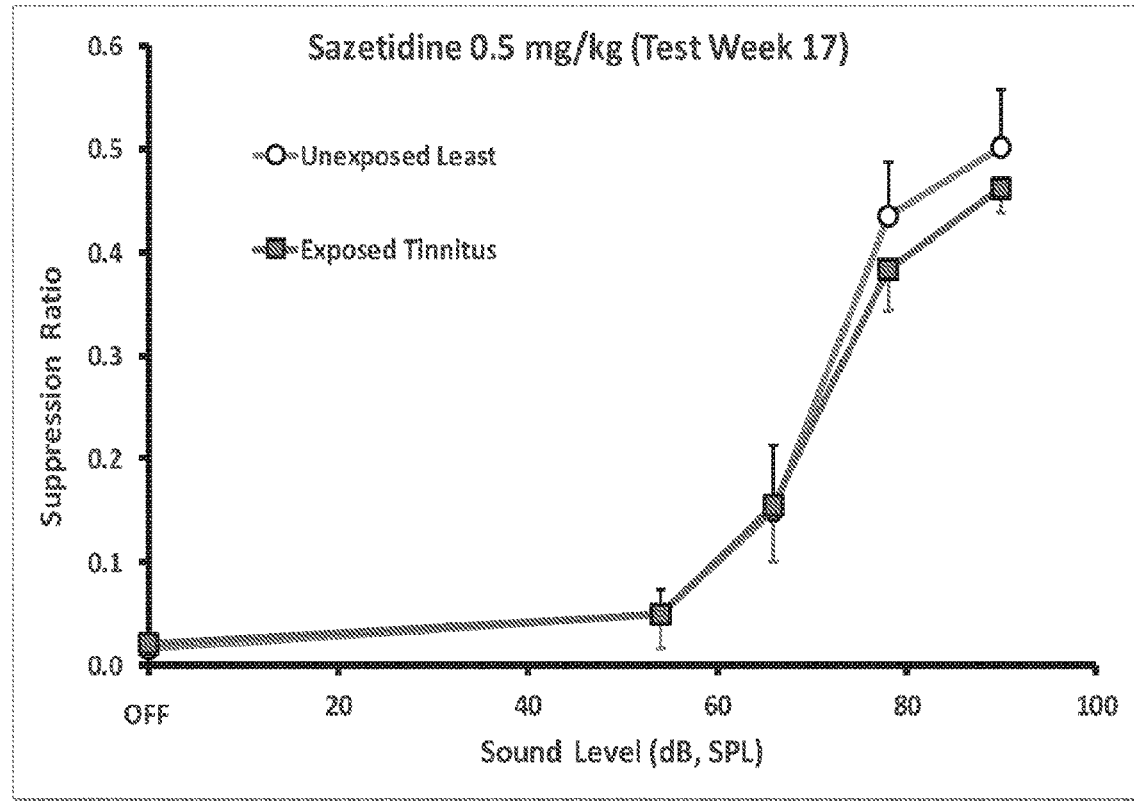
FIG. 8 shows the therapeutic effect of 0.5 mg/kg SC sazetidine with the suppression curve for animals with behavioral evidence of tinnitus no longer significantly different than the curve from the unexposed controls. This result suggests a tinnitus therapeutic effect at a lower dose. Statistical analysis: $F_{1,32}=2.63$, $p=0.1147$, $p'=0.623$.
Figure 9:
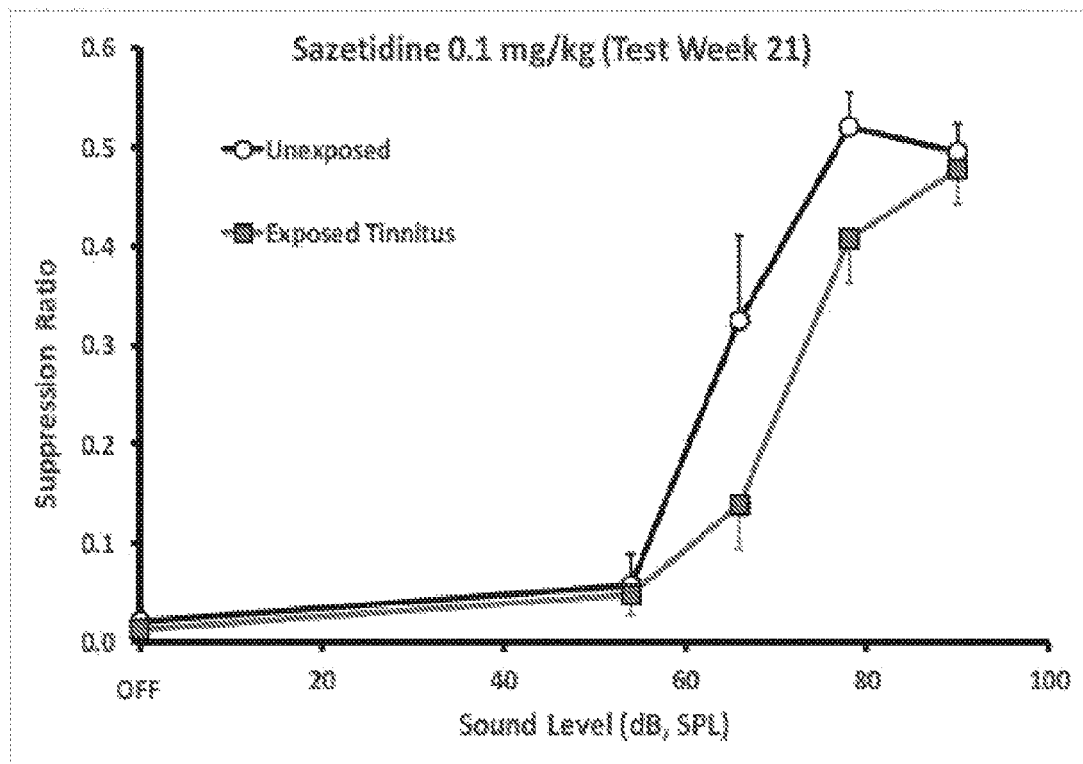
FIG. 9 shows a potentially weak therapeutic effect of 0.1 mg/kg SC sazetidine with graphical evidence of tinnitus while statistically the difference between groups was ambiguous after twenty-one weeks of tinnitus testing. Statistical analysis: $F_{1,32}=6.72$, $p=0.0142$, $p'=0.1209$.
Figure 10:
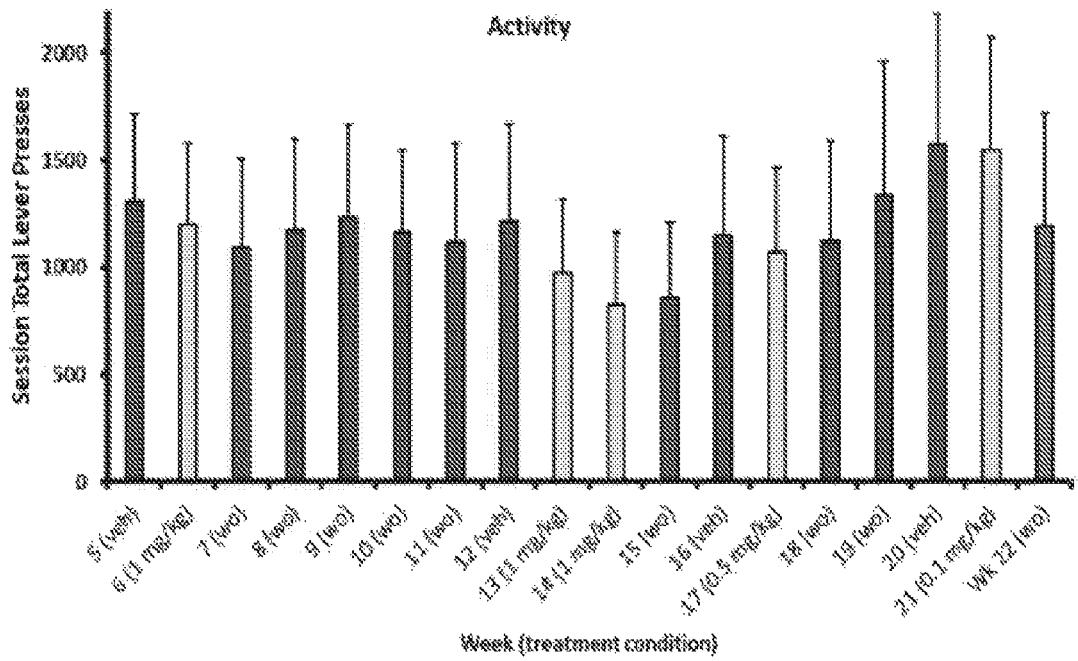
FIG. 10 illustrates the data for a non-specific effect. The non-specific effects appeared 10 to 15 min after treatment but were not present 1 hr after treatment, i.e., at the beginning of the test period. The decrease in session lever pressing at higher doses shows that there was some general sedation.

The washout series is summarized in FIG. 4. Sazetidine A, administered by SC injection, at a dose of 0.5 mg/kg, effectively and significantly decreased evidence of tinnitus although the therapeutic effect appeared somewhat less effective than at 1.0 mg/kg (see FIGS. 8 and 11). Sazetidine A, administered by SC injection, at a dose of 0.1 mg/kg, significantly reduced evidence of tinnitus although the therapeutic effect appeared smaller than the two higher doses shown in FIGS. 9 and 11. Non-specific drug effects are summarized in FIG. 10, which were evident at 1 mg/kg. At 1 mg/kg. There was visual evidence of excess salivation in about a third of the animals at 1.0 mg/kg. Within 10 min of drug treatment all animals assumed a prone resting position in their home cage, which lasted about 10 min. Afterward animals resumed normal cage activity, e.g., moving about, grooming, sniffing One animal (out of 16), sound-exposed without evidence of tinnitus, showed drug-dependent agitation, i.e., became difficult to handle, spontaneously vocalized even when not handled, and displayed exaggerated negative reactions to restraint. This behavior was not observed in washout or saline (vehicle) sessions, nor was it observed in the remaining 15 animals. Mild sedation was indicated by a decrease in total bar pressing at 1.0 mg/kg (FIG. 10).

Figure 11:
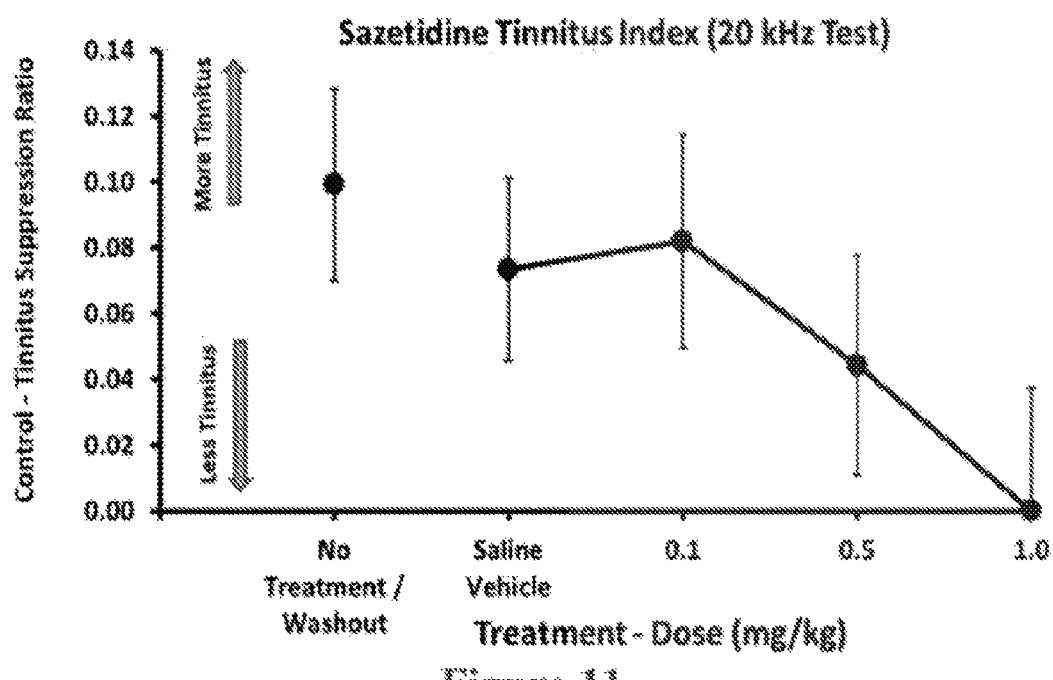
FIG. 11 shows the tinnitus close-response curve of sazetidine administration to animals with behavioral evidence of tinnitus. Therapeutic effect increased with dose seen as a decline in the tinnitus suppression ratio, i.e., tinnitus decrease, as the sazetidine dosage treatment was increased from 0.1 mg/kg to 1.0 mg/kg.

FIG. 11 shows that the effective dose level of sazetidine begins to show statistical effectiveness at about 0.5 mg/kg. The effectiveness increases as the dose is increased to about 1.0 mg/kg. It is hypothesized that the dose amount could be increased above 1.0 mg/kg to a level where toxicity risks begin to out-weigh the benefits of an increased dose amount.

Figure 12:
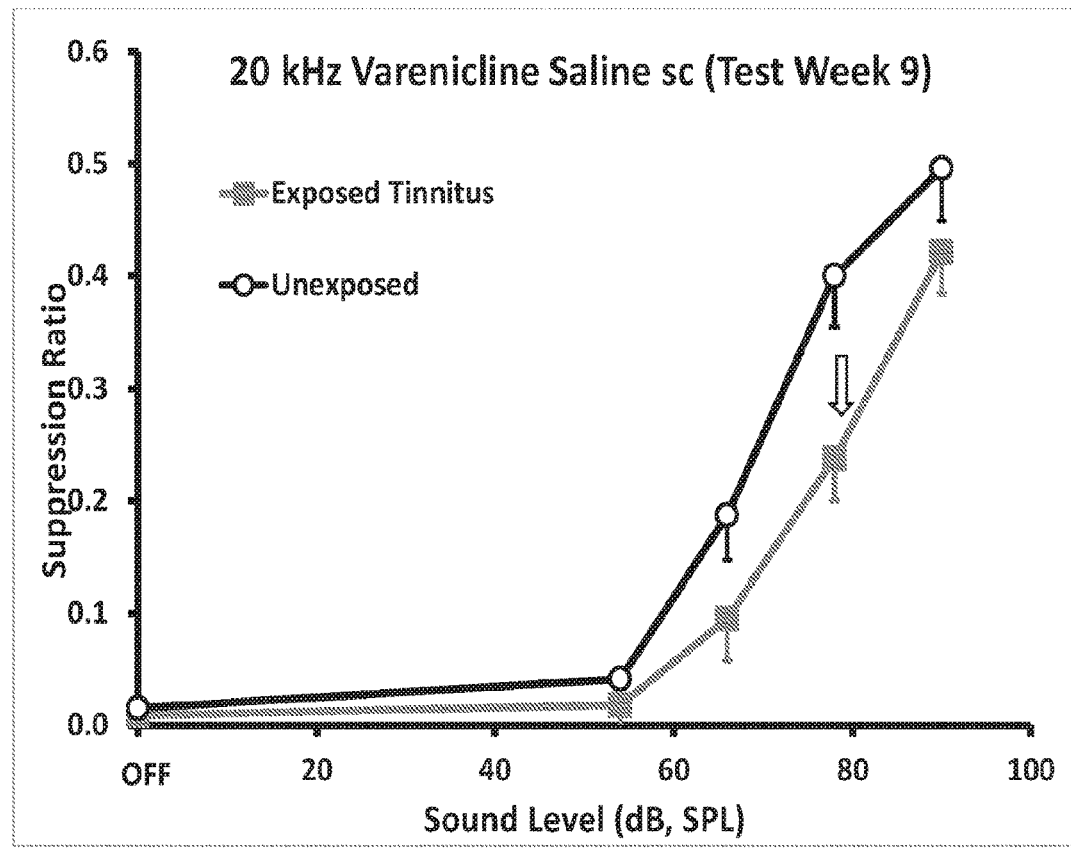
FIG. 12 illustrates significant evidence of tinnitus (arrow indicating down-shifted function) following sound exposure and prior to the first dose of varenicline. Animals with behavioral evidence of tinnitus are compared to control non-sound exposed animals. Initial tinnitus tests used saline as the drug vehicle. For FIG. 12 and also FIG. 13, suppression curves used a 20 kHz background sound and represent average behavioral data from three sessions. The difference between the unexposed control and exposed-tinnitus group function was significant as indicated by a mixed analysis of variance ($F_{1,32}=12.47$, $p=0.0008$), where F is the statistic (subscript, degrees of freedom) and p is the probability of a random-chance difference.
Figure 13:
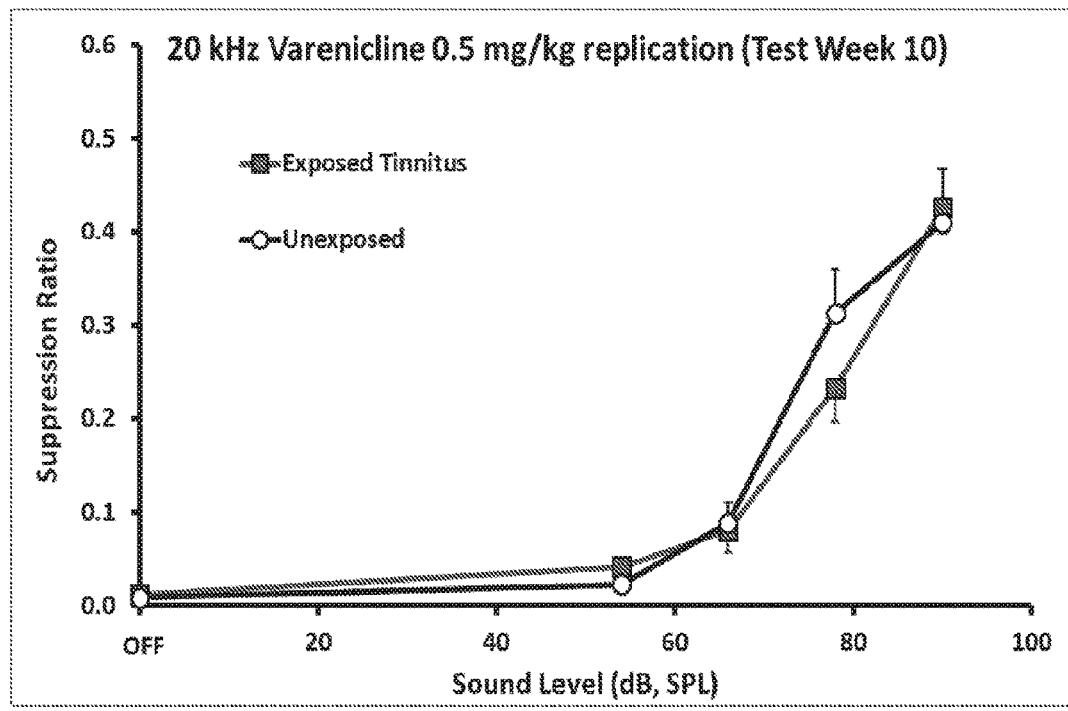
FIG. 13 shows replication of the therapeutic effect of 0.5 mg/kg SC varenicline with the suppression curve for animals with behavioral evidence of tinnitus no longer significantly different than the curve from the unexposed controls. This result suggests a tinnitus therapeutic effect at a lower dose 0.5 mg/kg varenicline.

FIGS. 12-13 show results for varenicline that are similar to the effects shown for sazetidine for treating a subject with symptoms of tinnitus. A dose of 0.5 mg/kg resulted in a 47% reduction of evidence of tinnitus in 12 animals with significant evidence of tinnitus compared to 8 unexposed controls. The tinnitus-reduction results were not-linear across varenicline doses between 0.1 and 1.0 mg/kg.

What is claimed is:

1. A method for treating a subject in need of treatment for tinnitus, the method comprising: administering to the subject a pharmaceutical composition comprising one or more pharmaceutically acceptable excipients and a therapeutically effective amount of sazetidine, varenicline, a pharmaceutically acceptable salt of sazetidine, a pharmaceutically acceptable salt of varenicline, or any combination thereof.

2. The method of claim 1, wherein the pharmaceutical composition contains sazetidine and/or varenicline in the form of tartarate, lactate, citrate, succinate, bisulfate, sulfate, phosphonate, hydrochloride, monohydrogen phosphate, dihydrogen phosphate, or any combination thereof.

3. The method of claim 1, wherein the pharmaceutical composition is administered as an oral formulation, as nasal drops or a nasal spray, as ear drops or an ear spray, topically, by intravenous injection, by intramuscular injection or by subcutaneous injection.

4. The method of claim 1, wherein the pharmaceutical composition comprises sazetidine and/or the pharmaceutically acceptable salt thereof.

5. The method of claim 1, wherein the pharmaceutical composition comprises varenicline and/or the pharmaceutically acceptable salt thereof.

6. The method of claim 1, wherein the pharmaceutical composition comprises sazetidine hydrochloride.

7. The method of claim 1, wherein the pharmaceutical composition comprises varenicline tartarate.

8. The method of claim 1, wherein the pharmaceutical composition comprises sazetidine and/or the pharmaceutically acceptable salt thereof, and the subject is administered a dose equivalent to from about 0.1 mg to about 2 mg of sazetidine free base per day.

9. The method of claim 1, wherein the pharmaceutical composition comprises sazetidine and/or the pharmaceutically acceptable salt thereof and the subject is administered a dose equivalent to 0.1 mg, 0.2 mg, 0.3 mg, 0.4 mg, 0.5 mg, 0.6 mg or 0.7 mg of sazetidine free base per day.

10. The method of claim 1, wherein the pharmaceutical composition comprises varenicline and/or the pharmaceutically acceptable salt thereof and the subject is administered a dose equivalent to from about 0.1 mg to about 2 mg of varenicline free base per day.

11. The method of claim 1, wherein the pharmaceutical composition comprises varenicline and/or the pharmaceutically acceptable salt thereof and the subject is administered a dose equivalent to 0.1 mg, 0.2 mg, 0.3 mg, 0.4 mg, 0.5 mg, 0.6 mg or 0.7 mg of varenicline free base per day.

12. The method of claim 1, wherein the pharmaceutical composition is administered orally.

13. The method of claim 1, wherein the pharmaceutical composition is administered orally in the form of a tablet, powder, a capsule, lozenges, chewables, syrup, or aerosol.

14. The method of claim 1, wherein the pharmaceutical composition is administered as nasal drops or spray or as ear drops or spray.

15. The method of claim 1, wherein the method further comprises monitoring the subject for adverse side effects.

\* \* \* \* \*